US005393228A

United States Patent [19]

Policicchio

[11] Patent Number: 5,393,228
[45] Date of Patent: Feb. 28, 1995

[54] DENTAL PROPHYLAXIS AND WATER CONSERVATION DEVICE

[76] Inventor: Piero A. Policicchio, 933 Butternut Dr., Holland, Mich. 49424

[21] Appl. No.: 154,033

[22] Filed: Nov. 18, 1993

[51] Int. Cl.⁶ ............................................... A61C 3/02
[52] U.S. Cl. ..................... 433/88; 601/165; 4/597; 4/625
[58] Field of Search ............... 433/80, 88; 601/162, 601/165; 4/596, 597, 602, 603, 625, 626, 627, 638; 51/436, 428

[56] References Cited

U.S. PATENT DOCUMENTS

| 3,882,638 | 5/1972 | Black . | |
| 3,971,136 | 7/1976 | Madsen | 433/88 |
| 3,972,123 | 8/1976 | Black . | |
| 4,111,193 | 9/1978 | Jousson | 601/162 |
| 4,174,571 | 11/1979 | Gallant | 433/216 |
| 4,214,871 | 7/1980 | Arnold | 433/216 |
| 4,253,610 | 3/1981 | Larkis | 239/430 |
| 4,412,402 | 11/1983 | Gallant | 51/439 |
| 4,462,803 | 7/1984 | Landgraf et al. | 433/88 |
| 4,776,794 | 10/1988 | Meller | 433/216 |
| 4,903,688 | 2/1990 | Bibby | 433/60 |
| 4,906,187 | 3/1990 | Amadera | 433/80 |
| 4,979,504 | 12/1990 | Mills | 601/165 |
| 4,984,984 | 1/1991 | Emrick | 433/80 |
| 5,094,615 | 3/1992 | Balley | 433/88 |
| 5,098,291 | 3/1992 | Curtis | 433/89 |
| 5,120,219 | 6/1992 | De Farcy | 433/88 |
| 5,165,456 | 11/1992 | Woolman | 141/98 |

Primary Examiner—Cary E. O'Connor
Attorney, Agent, or Firm—Harness, Dickey & Pierce

[57] ABSTRACT

A dental prophylaxis and water conservation device for in-home use. The device includes a tank coupled to the household water supply line and adapted to receive water which causes air contained within the tank to be pressurized. The water and air from within the tank are connected by lines to a handpiece which discharges both mediums simultaneously. Water leaving the tank passes through a container having an abrasive material which is picked up by the water and also discharged. The tank is further coupled to a plumbing fixture, such as a shower head. This enables the tank to be used as a water conservation device by allowing cold water to be purged from a hot water line into the tank, and subsequently used to provide water to the plumbing fixture. To recycle the purged water, the present invention entrains the water from within the tank as water from the supply line is being provided to the plumbing fixture.

13 Claims, 2 Drawing Sheets

DENTAL PROPHYLAXIS AND WATER CONSERVATION DEVICE

BACKGROUND AND SUMMARY OF THE INVENTION

This invention generally relates to a dental prophylaxis and water conservation device for home use. More particularly, the invention relates to a combination dental prophylaxis and water conservation device which is particularly suited to cleaning and providing prophylaxis of teeth, gingiva and other oral tissue while conserving purged cold water from a hot water supply line within the home.

Over the years, numerous dental devices have been proposed which provide prophylaxis through what is commonly referred to as a "sandblasting" technique. While sometimes intended for home use, these devices are more often only appropriate for office or clinical use because of the additional equipment needed for their operation. This equipment is both complex and expensive.

Generally, the above mentioned cleaning technique directs an abrasive laden fluid stream at the teeth, gingiva and other oral tissue. The abrasive stream cleans out food particles while removing plaque from the surfaces of the teeth and at the tooth/gingiva interface. Additionally, the devices stimulate circulation in the gingiva and oxygenate various anaerobic bacteria, both of which help to prevent periodontal diseases.

One of the first devices of the above mentioned type is disclosed in U.S. Pat. No. 3,972,123. The device of the '123 patent discloses a nozzle which ejects an abrasive laden air stream surrounded by a shroud of warm water. Improving on the '123 patent is U.S. Pat. No. 4,174,571. The '571 patent discloses the use of a water soluble abrasive in the air stream. Unfortunately, both of these systems are quite elaborate and therefore costly to produce, manufacture, purchase and maintain, all of which make them not particularly suited for home use.

One general problem with these particular types of devices is that the nozzle of the devices are susceptible to becoming clogged by the abrasive in the air stream and therefore require frequent maintenance. This problem has led to the development of numerous devices which utilize some variety of mechanism for agitating of the abrasive material in an attempt to prevent the discharge ports from becoming clogged. For obvious reasons, a device which is not susceptible to clogging without the added expense of an agitating mechanism is desirable.

U.S. Pat. No. 4,214,871 discloses the introduction of a soluble abrasive particle into the liquid stream which is discharged against the teeth and gingiva. In this device, water, at household pressures, is delivered through a nozzle that entrains the abrasive particles into the liquid stream (where they partially dissolve) and ejects them against the teeth and the adjacent oral tissues. Household water pressure, however, has proven to be ineffective at providing sufficient pressures for adequately removing plaque and other calculus. A greater force for propelling the liquid entrained particles is needed.

In U.S. Pat. No. 4,776,794, a pressurized pre-mixed abrasive slurry, is injected into a stream of compressed air and directed at teeth through a nozzle. An alternative embodiment of the '794 patent discloses a nozzle arrangement which uses compressed air to entrain the abrasive slurry rather than requiring a pressurized source of the slurry. From a practical standpoint, the device of the '794 patent is not readily adaptable to home use since it requires a separate pressurized air source and a pre-mixed abrasive slurry. This would require the home user to purchase a compressor or other expensive pressurized air source. Additionally, the device requires a costly pre-mixed material or the time consuming task of mixing the slurry to exact proportions of water, powder and surfactant. As with most consumer products, such a cost and labor intensive requirement detracts from its commercial viability.

As can be seen from the above discussion, the principal direction of technology in this field has been toward devices which are better suited for use in the professional dental office where the costs of the equipment necessary ,for providing compressed air and water are more easily afforded and recovered. Additionally, the prior devices are cumbersome since they require the use of specially prepared abrasives, such as finely milled sodium bicarbonate or an air/powder or water/powder suspension.

With the limitations of the prior art in mind, it is a principal object of this invention to provide a dental prophylaxis device which is particularly suited to use in the home of a patient for daily and thorough lavage of the teeth, gingival tissue and general oral cavity.

It is also an object of the present invention to provide a device which is adaptable to alternative uses within the home, including uses unrelated to oral hygiene. The present invention could be used, for example, to operate various other household items which perform scrubbing, spraying, dispensing, pumping, or other functions.

Another object of the present invention is to provide an in-home water conservation device which has as one of its features the ability to store and subsequently use purged water from a water supply line.

In general, the present invention is intended to be connected to a water supply line as is commonly found in the home. The invention uses purged water from the supply line to charge or generate a pressurized air source. A container, also in communication with the water supply line, receives powdered abrasive therein. The device is provided with a handpiece that includes a nozzle that is connected by lines to both the pressurized air source and abrasive container. During use, after the air pressure source has been charged or generated by the purged water from the supply line, a valve or valves in the handpiece are turned on to supply the air and the water. Water flowing through the container picks up the abrasive material and provides it to the nozzle where it is combined with and propelled by the pressurized air. The pressurized air imparts a higher projection force to the abrasive laden water thereby enabling it to more thoroughly clean the teeth, gingival tissues and oral cavity.

The water conservation aspect of the present invention can also be solely used as such in addition to assisting in teeth cleaning. When used in this manner, the device is connected to the water supply line, preferably a hot water line, of one of the household plumbing fixtures, such as a shower head, faucet, etc. When the fixture is turned on, the purged water from the water line is stored in a tank rather than being discharged, unused, down a drain merely because it is not at the desired temperature. Once the water from the supply line has reached the desired temperature, a valve on the inlet to the tank is switched so that the hot water is provided to the plumbing fixture. The water in the tank is then recycled and used to control the temperature of the water exiting the plumbing fixture.

Additional benefits and advantages of the present invention will become apparent to those skilled in the art to which this invention relates from the subsequent description of the preferred embodiments and the appended claims, taken in conjunction with the accompanying drawings.

DETAILED DESCRIPTION OF THE PREFERRED EMBODIMENT

Figures 1, 2:
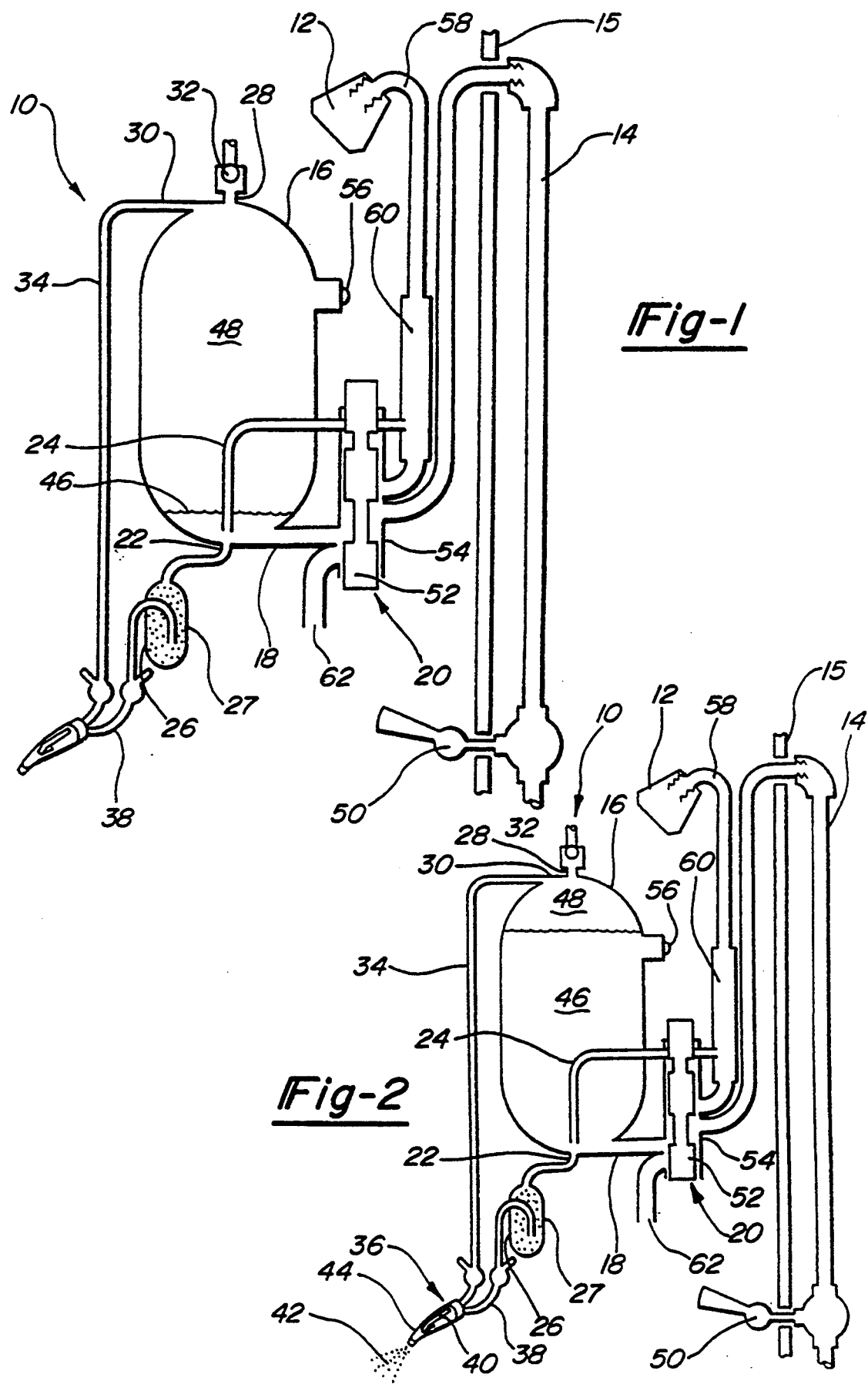
FIG. 1 is a diagrammatic illustration of one embodiment of the present invention prior to charging of the accumulator tank.
FIG. 2 is a diagrammatic illustration of the embodiment shown in FIG. 1 after charging of the accumulator tank and during use of the dental prophylaxis device.
Figure 3:
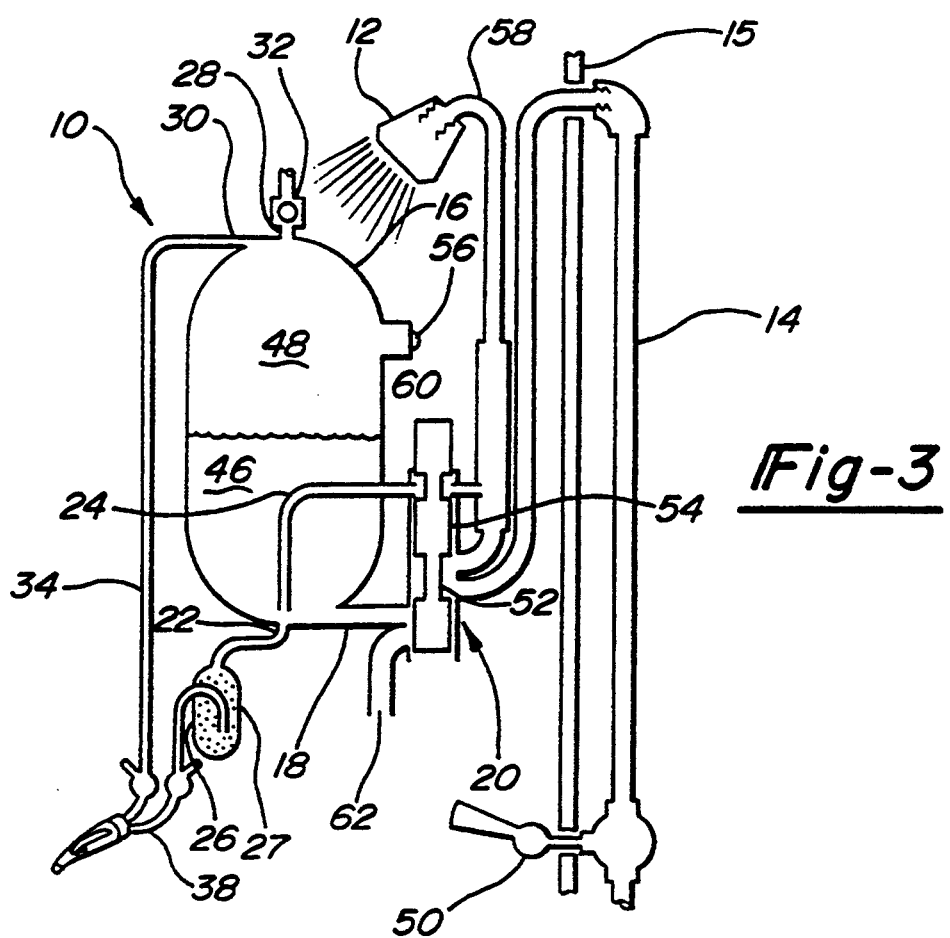
FIG. 3 is a diagrammatic illustration of the embodiment shown in FIG. 1 during use of the water conservation aspect of the present invention.

Referring now to the drawing, a dental prophylaxis and water conservation device incorporating the principles of the present invention is illustrated therein and generally designated at 10. The device is adapted for use with a household plumbing fixture 12, such as a shower head (illustrated), a faucet or other fixture, which is connected to a water supply line 14 within the home. As seen in the Figures, the water supply line is shown as extending from within a wall 15 to the present invention 10 and the plumbing fixture 12. While the present invention is particularly intended for use in conjunction with purged water from a hot water supply line 14, the device 10 could similarly be used with a cold water supply line. However, when used with a hot water supply line 14, it is believed that the device 10 will have its greatest utility since it will enable previously wasted cold water to be purged from the hot water line and stored for future use.

The dental prophylaxis and water conservation device 10 of the present invention includes an accumulator or pressure tank 16 which is, as mentioned above, adapted to receive and store purged cold water from the hot water supply line 14. As such, the tank 16 includes a water inlet 18 which is coupled by a valve 20 to the hot water supply line 14. The accumulator tank 16 also includes a pair of water outlets (hereinafter dental outlet 22 and fixture outlet 24). The dental outlet 22 is provided with an in-line container 26 adapted to store a water soluble abrasive, such as common household baking soda or sodium bicarbonate and/or other medicaments. The fixture outlet 24 is coupled through the valve 20 to the plumbing fixture 12.

While illustrated diagrammatically, it should be understood that the tank 16 could be positioned substantially anywhere desired. For example, the tank 16 could be located beneath a sink, above a shower head, within a cabinet or any other convenient location.

The accumulator tank 16 also includes an air inlet 28 and an air outlet 30. The air inlet 28 includes a check valve 32 (or other type of valve) for reasons which will become more readily apparent from the discussion which follows. The air outlet 30 is connected by an air line 34 to a handpiece 36 or other manipulable device. Also connected to the handpiece 36 is a liquid line 38 which extends from the handpiece 36 to the container 26 and which operates to deliver water and abrasive to the handpiece 36. While illustrated with the container 26 positioned apart from the tank 16 and handpiece 36, it should be understood that the container 26 could easily be incorporated as part of the tank 16 or the handpiece 36. In either event, this would not detract from the operability of the present invention and deemed to be within the scope of the invention.

While the illustrated embodiment is specifically intended to be used for dental prophylaxis, it should also be apparent that, by substituting various types of alternative handpieces for the illustrated handpiece 36, numerous devices having household utility could be operated. For example, the dental handpiece 38 could be replaced and the invention alternately used to operate a hand held scrubber, a sprayer, a dispenser, pumping device, or toy. In the interest of clarity, the present invention will only be specifically described as a handpiece 36 which is a dental prophylaxis appliance.

The handpiece 36 is provided with a trigger 40 which operates an internal valve mechanism (of a well known design such as a pinch valve) so that both air from the air line 34 and abrasive laden water from the water line 38 are simultaneously provided in a discharge 42 through a directable nozzle 44 on the end of the handpiece 36. The design of the nozzle 44 and the handpiece 36 are not specifically an aspect of the present invention and obviously would be of a construction based on both functional and aesthetic considerations. One requirement for the nozzle 44, however, is that the pressurized air is utilized to forcefully propel the abrasive laden water at the teeth and various tissues of the oral cavity. Additional features of this invention will become apparent from the discussion of the operation and use of the dental prophylaxis and water conservation device which follows.

To maximize use of the water conservation aspect of the present invention, it is recommended that the dental prophylaxis features be used immediately prior to and in conjunction with the use of hot water through the plumbing fixture 12, such as before taking a shower or before shaving. In this way, the cold water located in the hot water supply line 14, which has cooled since the last use of the plumbing fixture 12, can be purged from the hot water supply line 14, stored and subsequently used. Today, this purged cold water, which may constitute three to five gallons, is discarded down the drain without use solely because it is not of the desired temperature. By capitalizing on the observation that many people brush their teeth immediately prior to taking a shower or using the sink, this waste is alleviated by the present invention.

Prior to the dental prophylaxis and water conservation device 10 being used, it can be seen in FIG. 1 that the accumulator tank 16 is substantially empty of water (designated at 46). However, the tank 16 is full of air, generally designated at 48, which has been introduced into the tank 16 through the check valve 32 as the water level 46 receded during the previous use of the device 10. To initiate use of the device 10 of the present invention, a hot water valve 50 controlling the hot water supply line 14 is turned on and the valve 20 associated with the accumulator tank 16 is manipulated so that cold water being purged from the hot water supply line 14 is directed into the accumulator tank 16 as seen in FIG. 1.

The valve 20 can be any one of a well known variety of valves, but is illustrated as incorporating a sliding-type valve member 52 within a valve body 54, both of which cooperate to direct water flow selectively through multiple inlets and outlets. This is accomplished by providing the sliding valve member 52 with a varying diameter. Depending on its position within the slide body 54, the varying diameter of the valve member 52 allows different inlets to communicate with different outlets.

In FIG. 1, the water inlet 18 is in communication with the hot water supply line 14 which allows the accumulator tank 16 to fill with cold water 46 as it is purged from the hot water supply line 14. As a result of the tank 16 filling with the purged water 46, the air 48 within the tank 16 has less space to occupy and is compressed. The increased air pressure biases the check valve 32 so that the air pressure generated within the tank is not vented. Once the water 46 reaches a predetermined level within the tank 16 (depending on the amount of uncompressed air in the tank 16, the volume of the tank 16 and the amount of water needed to be purged), which not only purges cold water 46 from the supply line 14 but which also sufficiently charges or compresses the air 48 to provide an adequate amount of air pressure (preferably about 30 psi) for dental prophylaxis, an indicator switch 56 is tripped signaling that the device 10 is ready for use in cleaning the operator's teeth. The indicator switch 56 can be any one of a variety of mechanisms capable of performing this function and may be a switch operated by either the level of the water 46 or the pressure of the air 48 within the tank 16.

Once the indicator switch 56 signals that the tank 16 has been adequately pressurized and the cold water 46 purged, the user of the device 10 pulls the trigger 40 and manipulates the handpiece 36 to discharge pressurized air and abrasive water through the nozzle 44. The water is then ejected through the nozzle 44, atomized and propelled by the simultaneously provided air at a higher force.

When the handpiece 36 is triggered, water will flow through the dental outlet 22 of the tank 16 and into the container 26. In the container, the water 46 mixes with the abrasive 27, dissolving some of the abrasive 27 thereinto, before being delivered with the abrasive through the water line 38 to the handpiece 36. As mentioned above, baking soda is the preferred abrasive 27 and need not be of any special grade other than that purchased off the shelf at a grocery store by a typical consumer. Since the abrasive 27 is water soluble, any problems associated with clogging of the water line 38 or the nozzle 40 are substantially alleviated and non-existent. During dental prophylaxis, the valve 20 remains in its tank charging position so that additional water 46 is introduced into the tank 16 thereby maintaining substantially constant air pressure as water 46 as a lesser amount of water is removed from the tank 16 through the outlet 22.

The force provided by the combination of pressurized air 48 and the abrasive laden water 46 is sufficient to remove food particles, plaque, tarter and other dental calculus from the surfaces of the teeth, the areas between the teeth and the tooth/gingiva interface. Additionally, the air and water stream stimulates circulation in the gingival tissues and oxygenates various anaerobic bacteria thereby inhibiting periodontal diseases. Using baking soda as the abrasive also has the further effect of neutralizing the specific environment in which both the aerobic and anaerobic bacteria thrive.

After using the handpiece 36 and cleaning one's teeth, the valve 20 is moved to an off position where water from the hot water supply line 14 is prevented from communicating with the water inlet 18 of the accumulator tank 16 or with the fixture 12.

With cold purged from the hot water supply line and stored in the accumulator tank 16, the plumbing fixture 12 can now be used without wasting the purged water. When operated in this conservational mode, the valve 20 is moved so that the hot water supply line 14 communicates with a delivery pipe 58 of the plumbing fixture 12. Purged water 46 is then recycled by the fixture outlet 24 of the tank 16 which is also permitted by the valve 20 to communicate with the delivery pipe 58. More specifically, the delivery pipe 58 is provided with an aspirator or other mechanism 60 which uses the water going to the fixture 12 to entrain purged water 46 out of the accumulator tank 16. In this manner, the previously purged water 46 can actually be used to cool and regulate the temperature of the hot water now being provided by the hot water supply line 14 to the plumbing fixture 12.

It is possible that during use of the plumbing fixture 12, not all of the water 46 will be entrained from the tank 16. For this reason, the device 10 of the present invention is also provided with a drain 62. The drain 62, which may be another fixture such as a faucet, also communicates through the valve 20 with the tank 16. When the drain 60 is used, the water inlet 18 operates as an outlet.

As an alternative embodiment, other medicaments (either liquid or dry) could be added to the container 26 in addition with the abrasive, or alone, to be delivered through the water supply line 38. Further, the materials could be provided so that they would be delivered through the air supply line 34.

While the above description constitutes the preferred embodiments of the present invention, it will be appreciated that the invention is susceptible to modification, variation and change without departing from the proper scope and fair meaning of the accompanying claims.

I claim:

1. An abrasive supply apparatus which uses water from a household water supply line, said apparatus comprising:
    attaching means for connecting said apparatus to the water supply line;
    air supply means for providing a supply of pressurized air, said air supply means including an air outlet;
    discharge means for controlling and discharging air from said air supply means, said discharge means including a conduit connected to said air outlet of said air supply means; and
    a receptacle adapted to receive an abrasive material therein, said receptacle being in communication with the water supply line so that water can flow into and out of said receptacle, said abrasive material being carried by the water out of said receptacle, said discharge means also controlling and discharge water carrying said abrasive from said receptacle.

2. A pressurized air supply apparatus as set forth in claim 1 wherein said air supply means includes a pressure regulating means for maintaining a substantially constant source of air pressure during use of said apparatus.

3. A pressurized air supply apparatus as set forth in claim 1 wherein said abrasive material is baking soda.

4. An in-home water conservation device for use with a plumbing fixture connected to a water supply line, said water conservation device comprising:
- a tank for receiving and storing water therein, said tank having an inlet connected to the water supply line, said tank adapted to receive and store an amount of water from the water supply line, said tank also including an outlet in communication with the plumbing fixture;
- inlet valve means associated with said inlet and the water supply line, said inlet valve means for alternately diverting water from the water supply line into said tank and directing water from the water supply line to the plumbing fixture;
- outlet valve means associated with said outlet and the plumbing fixture, said outlet valve means for alternately obstructing or permitting the flow of water from within said tank to the plumbing fixture; and
- recycling means for removing water from said tank through said outlet and delivering said water to the plumbing fixture, said recycling means being operable when said inlet valve means is directing water from the water supply line to the plumbing fixture thereby mixing said water from within said tank with water from the water supply line and providing mixed water for use through the plumbing fixture.

5. A water conservation device as set forth in claim 4 wherein said tank is adapted to receive water in an amount sufficient to purge water of an undesirable temperature from the water supply line.

6. A water conservation device as set forth in claim 5 further comprising indicator means for indicating that water of an undesirable temperature has been purged from the water supply line.

7. A water conservation device as set forth in claim 5 wherein said recycling means entrains water from said tank through the use of water directed to the plumbing fixture from the water supply line.

8. A water conservation device as set forth in claim 4 wherein said recycling means is an aspirator coupled to the plumbing fixture and through which water directed to the plumbing fixture flows.

9. A dental prophylaxis and water conservation device connectable to a home plumbing fixture and a household hot a water supply line, said device comprising:
- attaching means for connecting said device to the hot water supply line;
- an accumulator tank having a water inlet coupled to the hot water supply line, said tank adapted to receive and store an amount of water from the hot water supply line sufficient to purge water of an undesired temperature water from the water supply line, said tank including a water outlet in communication with the plumbing fixture, said tank also including air pressure means for generating a supply of pressurized air within said tank in response to receiving purged water from said water supply line therein;
- an inlet valve associated with said water inlet and the water supply line, said inlet valve for alternately diverting purged water from the hot water supply line into said tank and directing non-purged water from the hot water supply line to the plumbing fixture;
- an outlet valve associated with said tank outlet and said plumbing fixture, said outlet valve alternately obstructing or permitting the flow of purged water from said tank to the plumbing fixture; and
- recycling means for removing purged water from said tank through said water outlet and delivering said purged water to the plumbing fixture and providing said purged water for use through the plumbing fixture;
- a receptacle adapted to receive an abrasive material therein, said receptacle including a receptacle inlet in communication with said tank and the water supply line to receive water therefrom into said receptacle, said receptacle also having a receptacle outlet through which water and can flow out of said receptacle and a portion of said abrasive material being carried by the flow of water;
- a handpiece connected to receive air from said air pressure means and to receive water from said receptacle outlet, said handpiece adapted to simultaneously discharge a stream of air, water and abrasive material and including a nozzle capable of directing said stream toward the teeth of a person;
- a valve controlling the amount of air received from said air supply means; and
- a valve controlling the amount of water received through said receptacle.

10. A water conservation device as set forth in claim 9 wherein said air supply means includes pressure regulating means for maintaining a substantially constant source of air pressure during use of said dental prophylaxis device, said pressure regulating means providing water to said air supply means at a rate generally corresponding to the amount of air and water provided to said nozzle and received from said air supply means.

11. A water conservation device as set forth in claim 9 further comprising indicator means for indicating when a predetermined amount of air pressure has been generated within said tank.

12. A water conservation device as set forth in claim 9 wherein said recycling means entrains water from said tank utilizing water directed to the plumbing fixture.

13. A water conservation device as set forth in claim 9 wherein said recycling means delivers said purged water to the plumbing fixture when said inlet valve directs non-purged water from the water supply line to the plumbing fixture thereby mixing said purged water with the non-purged water.

* * * * *